(12) United States Patent
Hollars et al.

(10) Patent No.: US 7,076,092 B2
(45) Date of Patent: Jul. 11, 2006

(54) HIGH-THROUGHPUT, DUAL PROBE BIOLOGICAL ASSAYS BASED ON SINGLE MOLECULE DETECTION

(75) Inventors: Christopher W. Hollars, Brentwood, CA (US); Thomas R. Huser, Livermore, CA (US); Stephen M. Lane, Oakland, CA (US); Rodney L. Balhorn, Livermore, CA (US); Olgica Bakajin, San Leandro, CA (US); Christopher Darrow, Pleasanton, CA (US); Joe H. Satcher, Jr., Patterson, CA (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 590 days.

(21) Appl. No.: 10/170,876

(22) Filed: Jun. 12, 2002

(65) Prior Publication Data

US 2006/0062440 A1 Mar. 23, 2006

Related U.S. Application Data

(60) Provisional application No. 60/298,584, filed on Jun. 14, 2001.

(51) Int. Cl.
*G06K 9/00* (2006.01)
(52) U.S. Cl. .................................................. 382/133
(58) Field of Classification Search ................ 382/129, 382/133; 702/21
See application file for complete search history.

(56) References Cited

U.S. PATENT DOCUMENTS 4,979,824 A 12/1990 Mathies et al.

5,961,924 A * 10/1999 Reichert et al. ......... 422/82.11
6,608,918 B1 * 8/2003 Rushbrooke et al. ....... 382/133

FOREIGN PATENT DOCUMENTS

WO     WO 99/40416 A1    8/1999

OTHER PUBLICATIONS

Princeton Instruments Datasheet for Pentamax-512EFT camera, p. 28, http://depts.washington.edu/keck/512eft.pdf.*
W. Trabesinger et al, Analytical Chemistry, 2001, 73, 110-1105.
Y. Ma et al. Analytical Chemistry, 2000, 72, 4640-4645.
W.A. Lyon et al, Analytical Chemistry, 1997, 69, 3400-3405.
F. Loscher et al. Analytical Chemistry, 1998, 70, 3202-3205.
C. Zander et al, Chemical Physics Letters, 286 (1998) 457-465.

* cited by examiner

*Primary Examiner*—Jingge Wu
*Assistant Examiner*—Ashutosh Upreti

(57) ABSTRACT

A method and apparatus with the sensitivity to detect and identify single target molecules through the localization of dual, fluorescently labeled probe molecules. This can be accomplished through specific attachment of the taget to a surface or in a two-dimensional (2D) flowing fluid sheet having approximate dimensions of 0.5 μm×100 μm×100 μm. A device using these methods would have $10^3$–$10^4$ greater throughput than previous one-dimensional (1D) microstream devices having 1 μm$^3$ interrogation volumes and would for the first time allow immuno- and DNA assays at ultra-low (femtomolar) concentrations to be performed in short time periods (~10 minutes). The use of novel labels (such as metal or semiconductor nanoparticles) may be incorporated to further extend the sensitivity possibly into the attomolar range.

20 Claims, 2 Drawing Sheets

HIGH-THROUGHPUT, DUAL PROBE BIOLOGICAL ASSAYS BASED ON SINGLE MOLECULE DETECTION

RELATED APPLICATION

This application relates to U.S. Provisional Application No. 60/298,584 filed Jun. 14, 2001 and claims priority thereof.

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to high-throughput methods and apparatus for ultra-sensitive biological assays with sufficient sensitivity to detect and identify single biomolecules. More particularly this invention relates to the detection of single target biomolecules through the use of two or more probe molecules each labeled with distinctive optical tags (such as fluorescent molecules, plasmon resonant particles, or quantum dots) that, selectively and specifically, recognize and form bound complexes with the target. Present immuno-, protein, or DNA (without amplification by polymerase chain reaction (PCR) or related techniques) assays have sensitivity thresholds in the nanomolar to picomolar range. Assays performed using the present invention are capable of extending the threshold of detection to femtomolar or lower concentrations with practical measurement times of 1–100 minutes.

Present immuno-and DNA assays (without amplification) have sensitivity thresholds in the nanomolar to picomolar range. Researchers have attempted to improve the sensitivity by several orders of magnitude by employing newly developed single molecule optical microscopy detection methods. These attempts have been partially successful but at the moment appear to be limited by non-specific surface attachment of unwanted labels or by impractically long measurement times.

Considering previous work, Mathies et al, U.S. Pat. No. 4,979,824 issued Dec. 25, 1990, describes how to detect single fluorescent particles and molecules with a fluid flow stream. They used only single-probe fluorescent labels, which suffers from the following shortcoming. A washing step is required to remove all of the unbound probe molecules from the sample. If some of the unbound reporter remains in the sample container, they can be mistaken for the presence of the target molecules and thus give a false positive result. As described here, the rate of false positives can be dramatically reduced by the use of two probe molecules, each with its own distinctive label.

Mathies et al also demonstrates the use of a fluid flow stream to carry sample molecules through the interrogating region of the optical detection system. They however use a fluid geometry that is either a small diameter stream of fluid that has limited capability for moving a significant sample volume through the interrogation region in a reasonable time period, or they use a 2D fluid sheet in which the sample volume is interrogated by scanning the focal volume in the x and y directions across the sample. Again the length of time to perform this type of assay can be impractically long.

Trabesinge et al, Anal. Chem. 2001, 73, 1100–1105, point out the advantages of two-colors in their assays but do not employ a high throughput device for examining practical sample volumes in practical time periods. Additionally they do not use dual probes in their assay methods.

Ma et al, Anal. Chem. 2000, 72, 4640–4645; Lyon et al, Anal. Chem. 1997, 69, 3400–3405; and Zander et al, Chemical Physics Letters 286 (1998) 457–465, use two-colors with dual probes in a flow system but they use only a 1-D small diameter flow stream and do not achieve the same degree of throughput as can be achieved with the 2D flow stream and image detection described here.

Loscher et al, Anal Chem. 1998, 70, 3202–3205; and Erkisson et al, WO99/40416, Aug. 12, 1999, describe the use of single molecule detection for ultra sensitive assays but do not describe the use of dual probes or high throughput methods.

The prior art does not provide a method and apparatus for performing high throughput ultrasensitive bioassays at the single molecule level with low false positive backgrounds.

This invention applies to immunoassays where the target biomolecule is an antigen. The assay uses at least two specific antibodies that act as probes by strongly binding to the target antigen without binding to other biomolecules. The assay then consists of labeling the two (for instance) antibodies with distinctive optical tags that can then be individually observed with a sensitive optical detection method. If the detection method reveals that the two antibodies are spatially co-located within the resolution of the optical imaging system and the frequency of co-localization events is greater than expected from random coincidence, the assay is positive for the presence target antigen and allows for a quantitative measure of its concentration.

We describe two optical detection methods for determining co-location of two or more optically labeled probe molecules. The first is an apparatus and method in which target antigens are captured by an antibody that has previously been attached to a solid surface substrate. The presence of the labeled antibodies is determined by scanned or wide-field imaging of the substrate. A positive result for the presence of the antigen is then given by the binding of two additional monoclonal antibodies, each having a distinct optical label. The number of co-localized events must be above background number of accidental co-located optical labels. This method is limited in sensitivity by non-specific surface binding by the labeled antibodies.

The second apparatus and method uses a 2D flowing fluid sheet confined by a microfluidic channel. This apparatus also uses the co-location of two or more optical labels but is not limited by non-specific surface attachment of antibodies because the targets and antibodies are primarily entrained in the moving fluid and are not in contact with the surfaces. This method gives $10^3$–$10^4$ times greater throughput than previous 1D micro-stream devices (Mathies et. al.). Using this method, immunoassays at ultra-low (femtomolar and lower) concentrations can be performed in short time periods (10's of seconds to 10's of minutes).

In addition to immunoassays, these methods and apparatus can also be applied to assays of short (10–50 bases) DNA or RNA oligonucliotides having specific target sequences. Here two or more single strand DNA complements each having distinct optical labels are used to specifically bind to the single strand target DNA fragment. Yet, Another class of assays is the detection of specific proteins or protein complexes. Here two or more labeled proteins or small molecules that bind to the target biomolecule are used as probes.

The invention described here is able to perform high throughput binding assays at the single molecule detection limit with low background by using the following features:

a) Dual probes—This reduces the background due to non-specific binding of the probe molecules
b) 2 or more colors—Each probe is labeled with a spectrally distinct optical label
c) This assay does not require the target molecule be directly labeled. Its presence is determined by the detection of labeled affinity probes.
d) Large interrogation volumes are employed to facilitate high-throughput. This is accomplished by using wide-field video rate, amplified CCD imaging, total internal reflection and microfluidic 2D flow-channel fluid manipulation.

The term "probes" as used herein is defined as antibodies, oligonucleolides, or proteins, for example.

SUMMARY OF THE INVENTION

This invention applies to the field of chemical, medical and biological molecular assays. This invention could also be applied to the sensitive detection of bioterrorism and biowarfare agents, forensics, or as an analytical instrument for analysis of environmental samples or for drug discovery. In particular, it generally applies to any affinity assay.

Immunological assays are those that use special biomolecules called antibodies that are proteins produced in mammals in response to other biomolecules, chemicals, or microorganisms (called antigens) that are identified as posing a threat to the health of the animal. Monoclonal antibodies, a class of antibodies, have the property that they bind very specifically to the target antigen (that is they bind or attach themselves only to a specific binding site on the target antigen and, for the most part, to nothing else).

These antibodies are the basis of a large number of medical and biological assays. Most antibodies for human antigens are produced by injecting the human antigen into animals such as mice, rabbits, goats, or sheep. After the immunological response by the animal (antibody production to the injected antigen), the antibodies are harvested from the animal and used as the basis of the assays. The estimated sales market for these assays was over $42B/yr in the year 2000. For example, in the medical field immunological assays are used for identifying such things as the presence of bacterial or viral infection, cancer markers such as prostate or breast cancer, and the propensity for heart disease.

A significant fraction of the current immunological assays use fluorescent labels. In this scheme, certain fluorescent molecules such as fluorescein or rhodamine are chemically attached to the antibodies. These fluorescencent molecules (also called labels or tags) produce light of specific wavelengths (called the emission spectrum) when light of a shorter wavelength (called excitation light) is used to illuminate these molecules. These molecules are used because with the proper optical sensing equipment small numbers of these molecules can easily be shown to be present in a sample.

An example of the way fluorescent labeled antibodies are used is to form what is known as a sandwich type assay is shown in FIG. 1. Here two different antibodies for the target antigen are used. One of the antibodies is attached to a solid surface, usually the wall of the container or well plate that holds the sample. The second antibody has a fluorescent molecule attached to it. The sample (usually in liquid form) is introduced into the container with the labeled antibody. The sample is given time (usually 10s of minutes) to allow the target antigen (if present) to bind (incubate) with the antibodies. After the incubation period the free unattached labeled antibody molecules are washed away with a washing solution. The container is then optically examined to see if any of the labeled antibody remains. If the target antigen had been present it would both have bound to the surface (with the first antibody) and with the labeled antibody, thus forming the immobilized complex or "sandwich."

In most conventional commercial assays the concentration threshold of detection for the target antigen is limited by both the ability to detect small amounts of light and by the non-specific binding of labeled antibodies to the container surface or other materials in the sample (that is the antibodies bind to something other than the target antigen). The current invention allows improvements in both of these areas thus significantly lowering the concentration threshold of detection for the target antibody.

As described in detail below the first improvement comes from more sensitive light detection. This is accomplished by employing methods capable of visualizing single fluorescent molecules. This brings the detection level down to the limit of a single fluorescent molecule in contrast to conventional methods that require at a minimum between 1000 and 1,000,000 fluorescent molecules for detection. Thus the threshold for detection using this invention is reduced by this same factor (1000–1,000,000). Alternately other optical labels recently becoming available can also be used such as phosphorescent compounds, quantum dots (nanoparticles made of semiconductors), plastic beads filled with fluorescent molecules or metal nanoparticles also called plasmon resonance particles. All of these labels can further increase the sensitivity of the assay.

In addition, a further improvement in sensitivity is obtained by reducing the background level due to nonspecific antibody binding. This is accomplished by using a flow channel instead of immobilization on a solid surface. By using a flow channel in which the fluorescently labeled antibodies are detected as they flow through an interrogation volume, the surface of the flow channel can be prepared in such a way that prevents or minimizes the random attachment of antibodies that would then produce a false positive. It is important to note that even with the prepared surface if some antibodies attach themselves they can be distinguished by their lack of motion from others in the flowing sample. Moreover because these nonspecific attached antibodies remain in the interrogation volume they will typically photobleach within a few seconds and cease to emit a signal. Photobleaching is an irreversible light induced reaction that destroys the fluorescent properties of those molecules.

Most immunological assays have concentration sensitivity thresholds in the nanomolar range. This invention lowers this threshold to the 1–100 femtomolar range, or lower. This is important because many existing assays are insufficiently sensitive for practical use or require impractically long time periods to complete the assay. For example the present commercial assay for botulinum toxin has a concentration detection threshold of 1 nanomolar. A concentration of $1/10^{th}$ this amount is sufficient to kill a cow. With this invention the threshold can potentially be lowered to below 1% of the lethal concentration dose. In general most assays, even those that already have useful thresholds would benefit from lower detection thresholds. For example lowered thresholds for the assays for cancer markers could allow detection of cancer at an earlier stage and thus improve treatment outcomes.

In addition to the use of immunological assays, this invention could be used for the detection of short strands DNA molecules with specific sequences. Conventional sensitive DNA detection is generally performed using sample amplification by the polymerase chain reaction (PCR) where as few as a single DNA molecules having a specific sequence of interest can be replicated to produce more than billions of exact copies. These large numbers of DNA molecules can then easily be detected using common complementary probe techniques. PCR, in general, however can only amplify specific sequences when there is some prior knowledge of the sequence. Alternately nonspecific amplification can produce many copies of the target DNA molecule but will also amplify background DNA molecules that may interfere and perhaps prevent observation of the DNA of interest. Moreover some DNA molecules have been found to be difficult to amplify. Other samples containing the DNA of interest also contain chemicals that interfere with the replication process. For these reasons, it is important to have DNA assays that do not rely on amplification. The invention described here is capable, under the proper conditions, of detecting single DNA molecules of a specific sequence. This can be accomplished where complements of the target DNA molecule are labeled with fluorescent molecules. In direct analogy to the immunological assays, a positive signal is produced when the two labeled complements are seen to be colocalized and thus indicate the presence of the target DNA molecule.

It is an object of the present invention to provide immuno and DNA assays having ultra sensitivity thresholds in the femtomolar and attomolar range.

A further object of the invention is to provide an apparatus and method that can detect, identify and quantitate a target based on the detection of single target molecules trapped at an interface by the localization of two or more fluorescently labeled probe molecules.

A further object of the invention is to provide an apparatus and method that can detect, identify and quantitate single target molecules in a two-dimensional (2D) flowing fluid sheet by the localization of two or more fluorescently labeled probe molecules.

A further object of the invention is to provide a device using this method for use in biological assays that would have $10^3$–$10^4$ greater throughput for ultrasensitive assays than prior known one-dimensional (1D) micro-stream devices having ~1 $\mu m^3$ interrogation volumes.

Another object of the invention is to provide an apparatus and method that enables immuno-and DNA assays at ultra-low (femtomolar) concentrations to be performed in short time periods (10's of seconds to 10's of minutes).

Another object of the invention is to provide for the use of novel labels (metal or semiconductor) nanoparticles incorporated to further extend the sensitivity possibly into the attomolar range. Other optical labels that could be used with this assay include polymer beads containing phosphorescent compounds, fluorescent molecules, labels made of multiple materials that give unique optical signatures, and other labels familiar to those skilled in the art.

Another object of the invention is to provide an apparatus which uses a 2D flow stream that is imaged by a video-rate amplified CCD camera that produces 2D images of an approximate 0.5 $\mu m \times 100$ $\mu m \times 100$ $\mu m$ volume as it flows through a microfluidics structure, using laser light to illuminate fluorescent labels within the flow channel.

Other objects and advantages of the present invention will become apparent from the following description and accompanying drawing. The invention involves a method and apparatus for producing ultra-sensitive high-speed biological assays based on 2D flow cell detection of single molecules. The invention can detect and identify single fluorescent molecules in a 2D flowing fluid sheet having dimensions of 0.5 $\mu m \times 100$ $\mu m \times 100$ $\mu m$. The apparatus using this method has $10^3$–$10^4$ greater throughput than prior known 1D mirco-stream devices having 1 $\mu m^3$ interrogation volumes. This invention enables immuno-, protein, and DNA assays at ultra-low (femtomolar) concentration to be performed in short time periods (10's of seconds to 10's of minutes). Also by the use of novel labels (metal or semiconductor nano-particles and other optical labels familiar to those in the field) may be incorporated to further extend the sensitivity into the attomolar range.

The apparatus of the invention uses a 2D flow stream that is imaged by a video-rate amplified CCD camera that produces 2D images of an approximate 0.5 $\mu m \times 100$ $\mu m \times 100$ $\mu m$ volume as it flows through a microfluidics structure, using laser light to illuminate fluorescent labels within the flow channel and minimize emission from other regions.

BRIEF DESCRIPTION OF THE DRAWINGS

The accompanying drawings which are incorporated into and form a part of the disclosure, illustrate embodiments of the invention and, together with the description, serve to explain the principles of the invention.

DETAILED DESCRIPTION OF THE INVENTION

Figure 1:
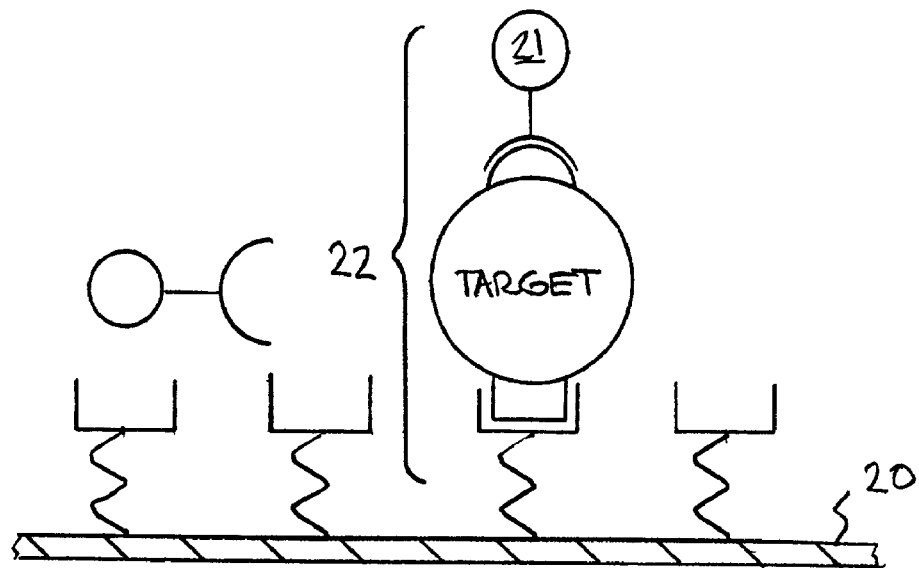
FIG. 1 schematically illustrates a typical approach to a sandwhich assay.

An example of the way fluorescent-labeled antibodies are used to form what is known as a one-color sandwich type assay is shown in FIG. 1. Here two different probes, defined as antibodies, oligonucleotides, or proteins, for the target antigen are used. One of the antibodies is attached to a solid surface (20), usually the wall of the container or well plate that holds the sample. The second antibody has a fluorescent molecule attached to it (21). The sample (usually in liquid form) is introduced into container with the labeled antibody. The sample is given time (usually 10s of minutes) to allow the target antigen (if present) to bind (incubate) with the antibodies. After the incubation period the free unattached labeled antibody molecules are washed away with some washing solution. The container is then optically examined to see if any of the labeled antibody remains. If the target antigen had been present it would both have bound to the surface (with the first antibody) and with the labeled antibody, thus forming the immobilized complex or "sandwich" (22). It should be noted that non-specifically bound labeled antibodies to the surfaces of the container or components can not be distinguished from the labeled antibody attached to the target of interest. This problem can be greatly alleviated by the use of dual probe labeling protocol as described below.

The importance of the dual probes is illustrated by the following: The probability of accidental co-localized events are estimated where P=Probability of non-specific surface attachment to a pixel (resolution element)

N=Total number of pixels examined by the assay

False positives in a one-color assay

PN

False positives in a two-color assay $P^2N$

So for example, if $N=10^6$ and $P=10^{-4}$, then the average number of false positives in a one color assay in $10^2$ where as in a two-color assay the number is $10^{-2}$ (1% chance of detecting a single false positive event).

Figure 2:
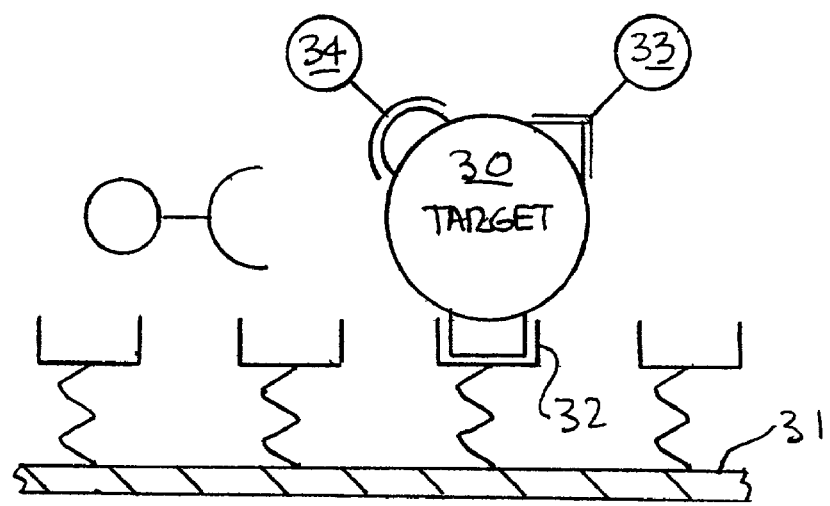
FIG. 2 schematically illustrates a two-color dual-antibody labeled sandwhich assay.

The present invention is directed to a method and apparatus for producing ultra-sensitive high-speed biological assays. One element of the invention is shown as an example in FIG. 2 where a schematic illustration of a two-color dual-antibody sandwich assay in which the target antigen (30) is attached to a surface (31) by a capture antibody (32). Two antibodies (33) and (34) labeled with different fluorescent dyes. Detection is performed by measurement of the colocalization or by fluorescence resonance energy transfer (FRET) using a scanning confocal or widefiled (total internal reflectance or epi) illuminatiaon techniques. In either case, fluorescent labels are said to be colocalized if they are measured to be in the same resolution element of the imaging system. This approach is applicable for some low detection limit analysis situations, but is still limited by the non-specifically bound probes to the capture surface.

Another element of the present invention is directed to a method and apparatus for producing ultra-sensitive high-speed biological assays based on 2D flow cell detection of single molecules. The method of this invention can detect and identify single fluorescent molecules in a 2D flowing fluid sheet having dimensions of approx. 0.5 µm×100 µm×100 µm, and enables immuno-and DNA assays at ultra-low (femtomolar) concentrations to be performed in short time periods (10's of seconds to 10's of minutes). Also, novel labels (metal or semiconductor nanoparticles) can be incorporated to further extend the sensitivity possibly into the attomolar range. The apparatus uses a 2D flow stream that is imaged by a video-rate amplified CCD camera that produces images of an approximate 0.5 µm×100 µm×100 µm volume as it flows through a microfluidics structure, using laser light to illuminate fluorescent labels within the flow channel and minimize emission from other regions. The apparatus is capable of high-speed single fluorescent molecule analysis ($10^3$–$10^4$ faster than previously used ID systems) and detection at femtomolar concentration levels in practical time periods (10's of seconds to 10's of minutes).

The microfluidic channel can be fabricated in a variety of substrates such as silicon or different kinds of glasses. The 0.5 micron thick observation part of the device is etched by reactive ion etching techniques (RIE) while the channels that lead to and out of it can be etched using either RIE or wet etching. The channels are closed on the top with a 100–200 micron thick glass. The glass is bonded thermally, anodically or by using a thin layer of glue such as cured PDMS (polydimethyldisiloxane). The velocity of the fluid through the observation channel is adjusted electrophoreticly or by controlling the pressure drop across the device or by controlling the flow rate out of a syringe pump.

The approach of this invention is to use a general immunoassay scheme having two or more distinct antibodies, chosen for high target specificity and large binding constants, that are labeled with spectrally distinct fluorophores (fluorescent molecules). The labeled antibodies are incubated in solution with the sample to allow attachment of the labeled antibodies to the target.

The flow is laminar with a parabolic velocity profile. The trajectories of the target molecules and labeled antibodies or DNA molecules are effectively plugged flow due to the transverse diffusion across the flow field.

Microscope Description:

Excitation light from a single or multiple light source(s) is directed to a Zeiss axiovert 200 inverted fluorescence microscope stand equipped with a alpha planfluar 1.45 NA oil immersion objective lens via either an epi illumination configuration with a directly coincident beam or totally internally reflected configurations. The use of a high numerical aperture objective is critical in this application in order to achieve an angle of incidence greater than the critical angle for a glass water interface as well as the most optimal collection of emitted photons from the fluorescently labeled species. An alternative approach would consist of an external total internal reflection configuration consistent with use of a prism located immediately above the fluidic device. In either scheme the fluorescence emission is collected using the high numerical aperture microscope objective and directed through a combination of optical filters that splits the collected image into multiple spectrally distinct images. These images are then collected with a Princeton Instruments Pentamax intensified CCD or similar camera.

For two-color surface-capture approaches, we used scanning confocal microscopy, the incubated sample being then brought into contact with a glass substrate to which a third "capture" antibody had been covalently linked through silane surface chemistry. The sample was scanned and a positive event was manifested as simultaneous emission detected in both fluorophore wavelength bands originating from the same point in the sample. This indicated two probes were co-localized to within better than 0.3 µm. The target molecule concentration was then determined based partly on statistical arguments showing that the number of detected co-localization of events exceeds the number of accidental co-localizations of lone antibody probes (i.e., probes not attached to a target).

We have found that non-specific binding is the major factor in determining the background level of the assay. As an alternative to surface attachment, we have studied freely diffusing molecules by forcing the excitation laser spot into a liquid. Rather than raster-scanning the spot spatially, here, the detection of a fluorescent molecule is provided through detection of short and intense photon bursts when the fluorescent molecules traverse the focal spot by diffusion. Simultaneous emission of a photo burst in both channels identifies a doubly labeled target molecule, while unbound antibodies or targets with one attached antibody are single channel events. Non-specific binding has been eliminated since no surfaces are involved. That scheme; however, is limited by the relatively slow diffusion time (picomolar concentrations show typically 10 positive events within one minute). The detection of a sufficient number of positive events at femtomolar concentrations to perform a realistic assay would thus take several days.

Previous devices of the schemes described above, have used systems in which samples are flowed through optical interrogated volumes of 1 µm$^3$. The apparatus of this invention uses a 2D flow stream and is illustrated in FIGS. 3 and 4.

Figure 3:
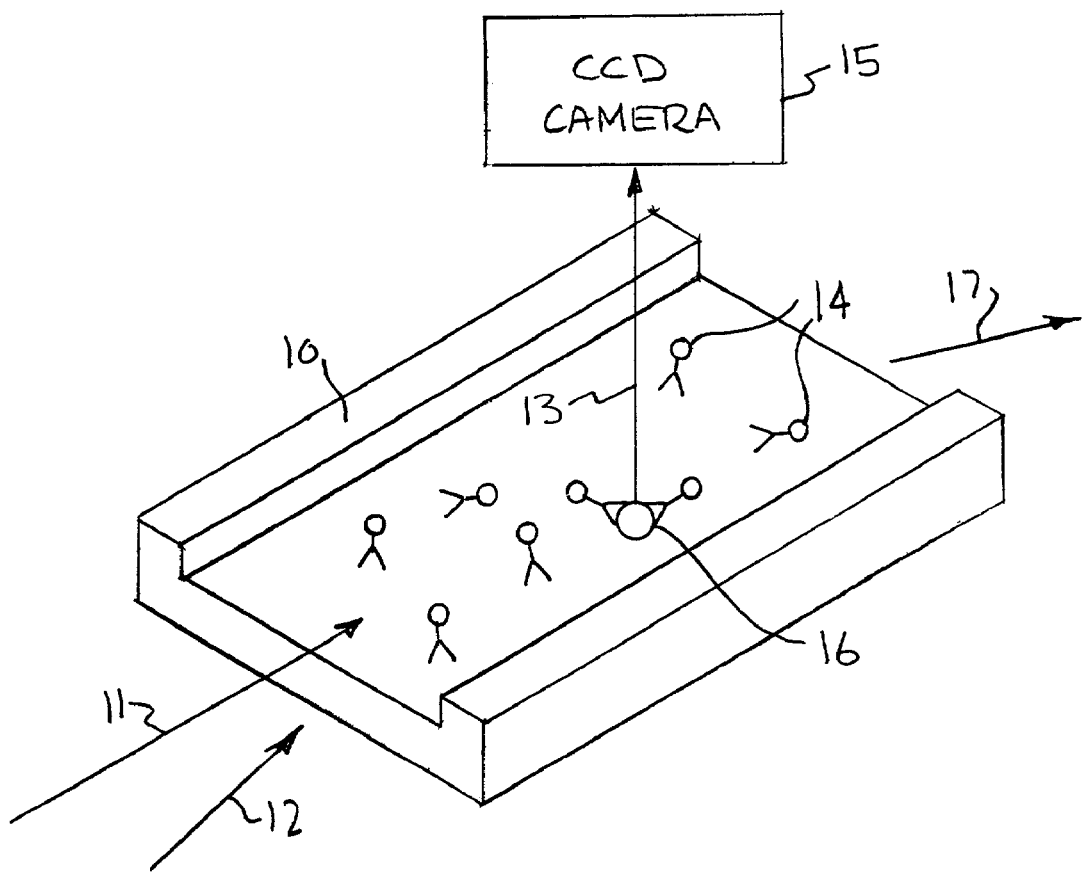
FIG. 3 schematically illustrates an embodiment of an apparatus for carrying out the described assay based on the detection of single fluorescent molecules in a 2d fluidic device.
Figure 4:
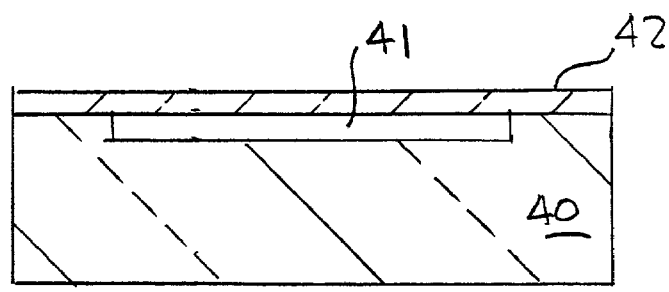
FIG. 4 schematically illustrates a crossection of the device described as FIG. 3.

FIG. 3 shows a planar microfluidic channel 10 (100 µm wide, 400 µm long, and 0.5 µm deep) through which a sample solution 11 flows. This channel 10 is illuminated by a slightly focused laser beam 12 in a total internal reflection (TIR) geometry. Fluorescence detection, indicated by arrow 13, of labeled antibodies 14 is based on an amplified CCD camera 15 that images a 100 µm×100 µm portion of the channel 10 in two colors. Positive events are characterized by the co-localized and simultaneous detection in each of the color channels, as indicated at 16. Arrow 17 illustrates reflected light of that of 12. The dimension of the depth of the observation region of the described device is determined both by the decay of the evanescent field (~400 nm for 514 nm radiation) when using TIR excitation and the restricted diffusion of the target molecules out of the sample focal plane (~1 □m) for the direct epi illumination configuration. FIG. 4 is a schematic illustration of a cross-section of the flow cell of FIG. 3 and consists of a glass or silicon cell body (40) having a micro fabricated flow channel (41). A cover plate (42) is attached to the top of the cell body (40) using a variety of methods including adhesives or glass—glass bonding.

Since we are making use of a parallel device (CCD camera), for example, this relates to a total detection time of 1 ms for a volume of 5000 μm$^3$ (100 μm×100 μm×0.5 μm). At a concentration of $10^{-15}$M, a volume of 0.1 μl contains approx. 600 target molecules. If every target molecule is identified through co-localization of two spectrally distinct dyes, 600 positive events are detected within 200s (3.3 minutes). This compares to roughly 4 days in standard assays for botulinum toxin, for example.

The sensitivity of the apparatus can be further increased by using novel optical labels (semiconductor or metal nanoparticles) that are capable of producing brighter optical signals. Specifically, these labels could consist of quantum dots that produce narrow-bands of fluorescent emission, or metal nanoparticles that are capable of strongly elastically scattering narrow wave-length bands from a white light source.

It has thus been shown that the present invention involves ultra-sensitive high-speed biological assays based on 2D flow cell detection of single molecules. This invention allows affinity assays at ultra-low (femtomolar) concentrations to be performed in short time periods (~10 minutes). With the use of novel labels (metal or semiconductor nanoparticles), the sensitivity can be further extended to possibly the attomolar range. The invention enables detection of low levels of water-borne or air-borne pathogens, either naturally occurring or man-made, as well as for chemical and medical assays for screening against various pathogens such as tumor markers, toxins, and other proteins or oligonucleotide sequences.

This assay approach could also have a direct impact into methods of drug discovery. Using nanopatterning techniques (such as dip pen nanolithography) with each spot consisting of a different species, this device would allow combinatorial assays requiring very little product in an extremely rapid high-throughput approach. Each nanopatterened spot (approx 500 nm) would correspond to a surface bound drug candidate that is suspected of binding to a specific protein or DNA sequence implicated in the treatment of a given illness. These spots would then be monitored as the fluorescently labeled target is flowing in solution. The level of binding would be determined by the intensity of the immobile fraction bound to each respective location. This approach would allow a drastic reduction in the amount of material needed for each of the chemical candidates, which are typically extremely expensive to produce. Furthermore, this analysis could be accomplished very rapidly, resulting in on the order of 100,000 spots per second.

Further application possibly lies in the areas of investigating antibody-antigen binding kinetics at low concentrations. This could be accomplished through monitoring the complexed (colocalized fluorescent signatures) and uncomplexed fractions of a flowing fluid. Knowing the relative concentrations of the antibody antigen species this can be used to determine binding constants at low concentrations. Additionally, binding dynamics and the isolation of the association and disassociation constants could be determined using a surface bound antibody or antigen and flowing the complement in the fluid of the channel. This could be accomplished by stopping the flow and monitoring the arrival and release of the free species in relation to the bound complement.

While the described device has a sensitivity sufficient to detect single fluorescent molecules, the device could also be implemented in a manner that use of multiple fluorescent labels.

The embodiment described employs a single assay. Other embodiments could implement multiple simultaneous assays by using a multiplicity of fluorescent labels. Additionally, the described embodiment uses two different markers. Other embodiments could use a single to multiple dye combinations at the expense or gain in sensitivity and specificity due to background and/or non specific binding. Furthermore, This embodiment uses the emission spectrum of the fluorescent or colored markers to identify the labels. Other embodiments could use other characteristics of the labels such as their fluorescent lifetimes.

While a particular embodiment, along with parameters, etc. has been described and/or illustrated to exemplify and teach the principles of the invention, such are not intended to be limiting. Modifications and changes may become apparent to those skilled in the art, and it is intended that the invention be limited only by the scope of the appended claims.

What is claimed is:

1. An immuno- and DNA assay apparatus, comprising:
   a microfluidic structure forming a two dimensional flow stream,
   a laser source configured to induce emission from one or more specific labeled probes configured with one or more fluorophores, said probes being disposed within the flow streams, and
   an amplified CCD camera for producing two dimensional images of positive events in the flow steam, wherein said positive events enable a specific target molecule to be identified due to the colocalization of between about 2 of said labeled probes configured with said one or more fluorophores to less than a hundred of said specific labeled probes configured with said one or more fluorophores.

2. The improvement of claim 1, wherein said laser light consists of a slightly focused laser beam in a total internal reflection or epi-illumination geometry.

3. The improvement of claim 2, wherein said laser beam additionally functions to minimize emission from other regions.

4. The improvement of claim 1, wherein said CCD camera produces two dimensional images of an approximate 0.5 μm×100 μm×100 μm volume as it flows through the microfluidic structure.

5. The improvement of claim 1, wherein said identified positive events in the flow stream comprises fluorescence detection of said specific labeled probes in the flow stream, said probes being selected from the group consisting of antibodies, oligonucleotides, and proteins.

6. The improvement of claim 1, wherein said CCD camera is constructed such that the fluorescence detection of said specific, labeled probes in the flow stream are imaged on said CCD camera as two or more images representing different spectral regions.

7. The improvement of claim 6, wherein said different spectral regions comprises two colors.

8. The improvement of claim 1, wherein said positive events are characterized by the co-localized and simultaneous detection in two or more of different colored channels of said CCD camera.

9. The improvement of claim 1, wherein assays at femtomolar concentrations or below are performed in a time period of not greater than about 100 minutes.

10. A method for detecting and identifying single fluorescent molecules in a 2D flowing fluid sheet, comprising:
 providing a microfluidic structure having a channel which includes at least an area of 0.5 μm×100 μm×100 μm,
 directing a sample flow having between about 2 specific labeled probes configured with one or more fluorophores to less than a hundred specific labeled probes configured with one or more fluorophores through said channel,
 illuminating said channel with a laser light beam, and
 specifically detecting said specific labeled probes using an amplified CCD camera so as to identify a specific target molecule.

11. The method of claim 10, additionally including forming the laser light beam so as to be slightly focused in a total internal reflection or epi illumination geometry.

12. The method of claim 10, wherein the amplified CCD camera produces 2D images of an approximately 0.5 μm×100 μm×100 μm volume as the sample flows through the channel of the microfluidic structure.

13. The method of claim 12, wherein the amplified CCD camera comprises a video-rate amplified CCD camera.

14. The method of claim 12, wherein the amplified CCD camera includes two or more images representing different spectral regions or colors.

15. The method of claim 10, wherein the detection is carried out using a CCD camera having two or more images representing different spectral regions or colors.

16. The method of claim 15, wherein detection of said specific labeled probes comprises positive events that are characterized by the co-localized and simultaneous detection in two or more different colored channels of said CCD camera.

17. The method of claim 11, additionally including adding to the sample flow semiconductor or metal nanoparticles capable of producing brighter optic signals, thereby extending the sensitivity into the attomolar or below ranges.

18. The improvement of claim 1, wherein said specific labeled probes reduces background due to non-specific binding.

19. The improvement of claim 18, wherein each said probe is labeled with a spectrally distinct optical label.

20. The method of claim 10, additionally including adding to the sample flow semiconductor or metal nanoparticles capable of producing the ability to analyze more targets simultaneously than are capable with fluorescently labeled probe combination.

* * * * *

UNITED STATES PATENT AND TRADEMARK OFFICE
CERTIFICATE OF CORRECTION

PATENT NO. : 7,076,092 B2 Page 1 of 1
APPLICATION NO. : 10/170876
DATED : July 11, 2006
INVENTOR(S) : Christopher W. Hollars et al.

It is certified that error appears in the above-identified patent and that said Letters Patent is hereby corrected as shown below:

Attorney, Agent, Or firm is missing. It should read:

*Attorney, Agent, or Firm* - Michael C. Staggs; L.E. Carnahan;

Alan H. Thompson

Signed and Sealed this

Seventeenth Day of October, 2006

JON W. DUDAS
*Director of the United States Patent and Trademark Office*